US007033839B1

(12) United States Patent
Dobler et al.

(10) Patent No.: US 7,033,839 B1
(45) Date of Patent: Apr. 25, 2006

(54) QUICK ACTING TOXIC AMMONIA TEST FOR AQUEOUS SAMPLES

(75) Inventors: Lydia J. Dobler, Elkhart, IN (US); Jean M. Gibbons, Elkhart, IN (US); Vladimir Yu Evtodienko, Moscow Region (RU)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 09/268,930

(22) Filed: Mar. 16, 1999

(51) Int. Cl.
*G01N 33/19* (2006.01)
*G01N 31/22* (2006.01)

(52) U.S. Cl. .......................... 436/113; 436/169; 422/56
(58) Field of Classification Search ................. 436/113, 436/167, 169; 422/56
See application file for complete search history.

(56) References Cited

U.S. PATENT DOCUMENTS

| 3,787,184 | A | * | 1/1974 | Novak et al. ................. 436/96 |
| 4,201,548 | A | * | 5/1980 | Tamaoku et al. ............ 436/113 |
| 4,223,089 | A | | 9/1980 | Rothe et al. |
| 4,548,906 | A | * | 10/1985 | Sikikawa et al. ............ 436/113 |
| 5,290,704 | A | * | 3/1994 | Chang ........................ 436/128 |
| 5,420,016 | A | | 5/1995 | Boguslaski et al. |
| 5,710,372 | A | | 1/1998 | Becket |
| 5,882,937 | A | | 3/1999 | Sauer et al. |
| 5,989,840 | A | * | 11/1999 | D'Angelo et al. .......... 435/7.32 |

FOREIGN PATENT DOCUMENTS

| EP | 0 481 436 A1 | 4/1992 |
| GB | 902884 | 8/1962 |
| WO | WO 97/35191 | 9/1997 |

OTHER PUBLICATIONS

W. Sellien et al., *Development of an optical–chemical sensor for the detectino of ammonium ions*, (1992)83–88, Analytica Chimica Acta, 269.
Martina Trinkel et al., *Study of the performance of an optochemical sensor for ammonia*, Analytica Chimica Acta 320 (1996) 235–243.
Perihan Caglar et al., *Ammonia–sensitive Fibre Optic Probe Utilising an Immobilised Spectrophotometric Indicator*, Analyst, Sep. 1987, vol. 112, pp. 1285–1288.
Kurt Seiler et al., *Design and Characterization of a Novel Ammonium Ion Selective Optical Sensor Based on Neutral Ionophores*, Analytical Sciences, Oct. 1989, vol. 4, pp.557–561.
F.L. Dickert et al., *Fiber–Optic Dipping Sensor for Organic Solvents in Wastewater*, Anal. Chem. 1989, 61, 2306–2309.
Satoshi Ozawa et al., *Ammonia–Gas–Selective Optical Sensors Based on Neutral Ionophores*, Anal. Chem. 1991, 63, 640–644.
Steven J. West et al., *Selective Ionophore–Based Optical Sensors for Ammonia Measurement in Air*, Anal. Chem. 1992, 64, 533–540.
Tobias Werner et al., *Ammonia–sensitive Polymer Matrix Employing Immobilized Indicator Ion Pairs*, Analyst, Jun. 1995, vol. 120, pp. 1627–1631.
W. Fresenius et al., *Water Analysis*, Deutsche gesellschaft fur, Technische Zusammenarbeit (GTZ) GmbH, 6236 Eschborn 1, FRG, 1988, pp. 285–292.

\* cited by examiner

*Primary Examiner*—Jill Warden
*Assistant Examiner*—Latoya Cross
(74) *Attorney, Agent, or Firm*—Barnes & Thornburg

(57) ABSTRACT

A method, test reagent and device usable as a test strip for detecting toxic ammonia levels in water samples such as aquarium water. The volume of the water to be tested contacted with a soda lime reagent to raise the pH to at least 10, and simultaneously contacted with a hydrophobic barrier membrane capable of allowing only ammonia gas to pass through. The membrane is coated with a pH chromogenic indicator mixture which changes color if ammonia gas passes through. The color response of the sample is compared with standard color charts to determine the toxic ammonia potential.

12 Claims, 2 Drawing Sheets

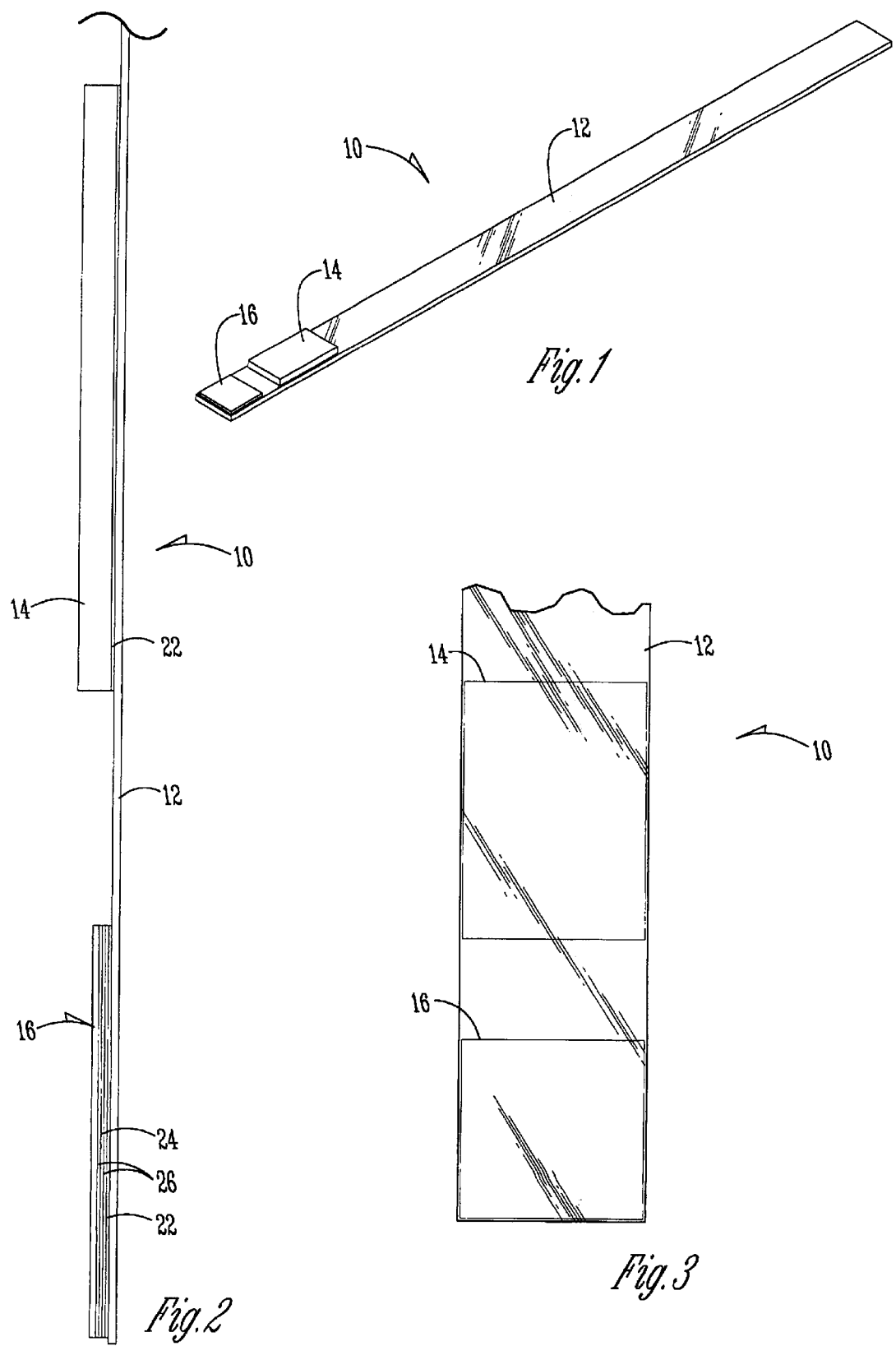

QUICK ACTING TOXIC AMMONIA TEST FOR AQUEOUS SAMPLES

FIELD OF THE INVENTION

This invention relates to a method, reagent and test device suitable for testing the levels of toxic ammonia potential for water, in particular in aquariums.

BACKGROUND OF THE INVENTION

Aquariums represent one type of closed environment in which production of ammonia naturally occurs. Those natural occurrences are the decomposition of plants, dead fish, uneaten food and waste excreted by the fish. In nature, the problems of ammonia accumulation are often solved by a biological process called the nitrogen cycle. That is, the ammonia is converted through nitrite to nitrate, which can then be used by the plants in the water. While this cycle does occur in aquariums, ponds or septic tanks, the equilibrium is heavily shifted in favor of ammonia production because of the limited, confined environment. As a result, ammonia levels rise.

Toxic ammonia, at levels of from as low as 0.01 ppm to 0.02 ppm for sustained periods can kill fish! As a result, more often than not when an unsuspecting aquarium owner finds dead or dying fish, it is a result of production of high levels of ammonia within the aquarium tank.

Aquarium owners have several options available to them in order to avoid a rise in dissolved ammonia gas level in the tank. For example, frequent water changes, and efficient chemical and biological filtration often can be used to keep ammonia in check. However, unless one can measure the amount of ammonia potential in a given tank, the owner is literally in the dark as to whether or not there is an increased risk of a fish kill by toxic ammonia. For this reason, ammonia has sometimes been referred to as the invisible killer of aquarium fish.

For many years, various methods of monitoring ammonia concentrations have been available. The most frequently used methods are based on chemistries that make use of Nesslers reagent or Salicylate. These methods typically involve mixing chemicals and waiting 5–20 minutes for a result.

Traditional methods involve the use of liquids, powders or tablets. Liquid test kits have the benefit of being easy to mix. However, liquid reagents are, in general, unstable and lose their accuracy rapidly over time. Also, some of the liquids used are toxic, and the opportunity for spills and accidental ingestion is possible. Powder test kits are more stable and have an improved shelf life. They are easy to use but involve many steps, and accidental spills of dangerous chemicals can result when opening the sachets.

Of these forms of test kits, the safest to handle are probably those that involve the use of tablets. They are simple to use and have good chemical stability. It does, however, take time and effort to dissolve the tablets in the water sample, and a lengthy wait is still required before a reading can be taken.

It therefore can be seen that there is a real and a continuing need for the development of a quick-acting test for ammonia potential in aquariums. It is a primary object of this invention to fulfill this need.

Another object of the present invention is to provide a quick-acting test which is especially adapted for use with test strips, as opposed to loose powder, tablets, or liquid chemicals.

A yet further object of the present invention is to provide a test strip which can be used to test ammonia potential of aquariums or other water samples within one minute or less.

Another object of the present invention is to provide a quick-acting test which uses a chromogenic indicator which responsively and discriminatingly changes color upon contact with dissolved ammonia gas, and as such can be compared with standard color intensity charts to determine the potential for toxic ammonia of any given water sample.

Another example is to provide reagent strips which can be conveniently packaged in a simple container to increase shelf life and which are easy to use by consumers.

The method and manner of accomplishing each of the above objectives, as well as others, will become apparent from the following detailed description of the invention.

BRIEF DESCRIPTION OF THE DRAWINGS

FIG. 1 shows a perspective view of a test strip of this invention.

FIG. 2 shows a side view of a test strip of this invention.

FIG. 3 shows a rear view of a test strip of this invention.

SUMMARY OF THE INVENTION

A method, test reagent and device usable as a test strip for detecting toxic ammonia levels in water samples such as aquarium water are disclosed. The volume of the water to be tested is contacted with a soda lime reagent to raise the pH to at least 10, and simultaneously contacted with a hydrophobic barrier membrane capable of allowing ammonia gas to pass through. The membrane is coated with a pH chromogenic indicator mixture which responsively and discriminatingly changes color if ammonia gas passes through. The color response of the sample is compared with standard color charts to determine the toxic ammonia potential.

DETAILED DESCRIPTION OF THE INVENTION

Figure 4:
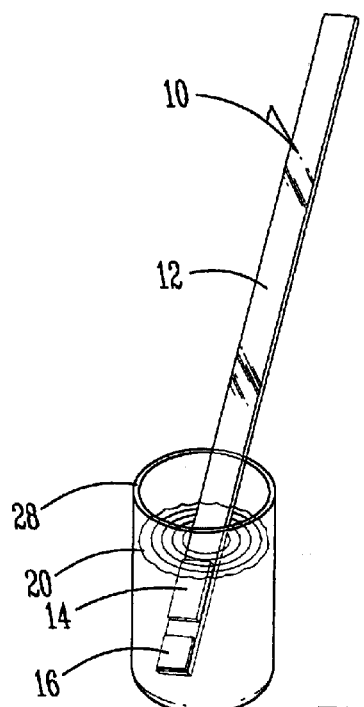
FIG. 4 shows a test strip of this invention placed inside of a small selected sample in the process of being dipped and swished to allow materials to escape from the soda lime reagent pad into the test sample, which can then be tested for ammonia gas that passes through the membrane to the indicator material.
Figure 5:
FIG. 5 shows a comparison chart using one responsive and discriminating indicator mix to correlate with parts per million of toxic ammonia.

Looking first at the drawings, it can be seen that this invention method can be most suitably performed with a test strip 10. Test strip 10 has a handle portion 12 and two pads 14 and 16. Pad 14 is a soda lime pad used to adjust the pH of a confined test sample (see FIG. 4), and indicator pad 16, which provides the color change in a high pH environment (at least 10). Alkalizing pad 14 and indicating pad 16 are bound to the handle portion 12 by adhesive 22. Indicator pad 16 is comprised of a hydrophobic membrane 24 with a coating 26. Hydrophobic membrane 24 as explained below is porous and allows ammonia gas to pass through the membrane. When the gas passes through the membrane, it contacts indicator on indicator pad 16 and changes color. It can be viewed from the back side (see FIG. 3), and the change in color, if it occurs, is known therefor to selectively occur because of the presence of ammonia gas, which is the only gas that passes through that is responsive to the indicator. The color change can then be compared to a standard comparative chart (see FIG. 5) for a determination of the parts per million of total ammonia. In this way, the toxic ammonia potential risk of an aquarium can be at least semi quantitatively assessed as to whether it is safe (light yellow color), or at high risk (light green) or somewhere in between.

Before discussing in detail the reagent system on the soda lime pad 14 and the indicator pad 16, certain constructional features of the test strips are worthy of mention. First, the handle 12 must be made of a clear, semi-rigid and inert plastic material. It must be clear so that an indicator change can be viewed from its back side (FIG. 3). The handle must be semi-rigid to provide sufficient rigidity so that the test strip can be dipped and swished with a confined sample (see FIG. 4). Many suitable polymeric substantially inert plastic materials could be used and will be apparent to one of ordinary skill in the art. However, one suitable material is clear polystyrene which can be purchased from American National Can Company. Soda lime pad 14 is made of a carrier paper matrix of high absorbency quality.

A preferred embodiment of the present invention involves the use of a carrier paper matrix for the soda lime pad 14. By using a carrier matrix such as bibulous paper to contain and carry to the test reaction sample 20 the pH adjusting system, it has been found that the pH of even highly buffered samples can be raised above 10.

In its simplest form, a piece of bibulous filter paper of sufficient porosity and capillary affinity to cause the fluid being tested to migrate into the paper is coated or otherwise incorporated with the soda lime pad 14. When the strip 10 is immersed into a sample 20 to be tested, the test sample 20 contacts the pad 14, and the soda lime dissolves into the test sample 20 to adjust pH. The net result of using such a strip is that the volume of the ammonium ion present is deprotonated to ammonia gas and made available to contact porous hydrophobic barrier membrane 24. The ammonia gas passes through membrane 24 to contact the indicator. The paper of pad 14 and membrane of pad 16 can be affixed to an inert handle 12.

A variety of papers can be used for soda lime pad 14. A preferred paper is Ahlstrom 939, which is a thick paper with high absorbency. This is preferred to deliver the maximum amount of base from soda lime pad 14 to test sample 20. During the impregnation, in fact the paper decreases in width, and this also aids in delivering the maximum amount of base by concentrating the amount of chemicals in the pad.

The purpose of soda lime pad 14, as can be seen, is to provide pH adjustment of the confined sample 20 selected from the test water and placed into test tube 28. The precise material used in the soda lime pad is not critical, except that it must be a water soluble base system to provide a pH in test sample 20 upon dipping and swishing for approximately 30 seconds, that is, at least 10. A pH of at least 10 in the defined sample 20 is required in order to provide deprotonation of ammonium ion in the test sample 20 to ammonia gas sufficiently to give an accurate result. It has been found that a suitable reagent mix for the soda lime pad 14 is a saturated solution of calcium carbonate with added sodium hydroxide which effectively impregnates pad 14 with a mix of calcium and sodium hydroxides and carbonates. Preferred amounts of sodium hydroxide to calcium carbonate are 2 molar sodium hydroxide (80 gram/l) and 1.0 gram/liter of calcium carbonate. When the test strip 10 is dipped into test sample 20, it should be vigorously moved with swishing of the strip and movement up and down in the water sample 20 for approximately 30 seconds, making sure all the time that the pads are submerged. During this time, the alkaline material moves out from pad matrix of soda lime pad 14 and dissolves in the test sample 20. This raises the pH, allowing the deprotonation of ammonium ion present to ammonia. Thus, any concentration of ammonium ion present in the aquarium test sample is converted to ammonia gas at a high pH.

If ammonia gas is present, it will come into contact during the dipping and swishing with hydrophobic membrane 24 of indicator pad 16. Porous hydrophobic barrier membrane can be purchased from a variety of sources. Hydrophobic membranes which would absorb the pH indicators include but are not limited to: Versapore-H (Pall-Gelman) (a hydrophilic acrylic copolymer with a hydrophobic surface treatment); PVDF (polyvinylidene fluoride) membranes; Fluorotrans (Pall-Gelman) Immobilon (Millipore) Nylon; Hydrolon (Pall-Gelman) PTFE-supported on polypropylene or polyester; Tetratex (BHA-Tex); and Polypropylene from CUNO. Such a membrane is fibrous, and has a high degree of porosity. One suitable membrane is a polypropylene membrane available from Cuno which is naturally hydrophobic, has high air permeability, low extractables, and a broad range of chemical resistance. Pore sizes for the membrane are available from a nominal 0.6 microns to 10 microns. Preferred pore size is from 0.2 microns to 2.5 microns, preferably 0.6 microns to 1.2 microns, and most preferably about 0.6 microns. Cuno Filter Systems, from which such membranes are obtainable, is located at 400 Research Parkway, Meridian, Conn. 06450 USA.

Conceivably, other alpha olefin polymeric inert hydrophobic barrier materials also can work for the present invention. This porous membrane, which is hydrophobic by nature of its property, is preferably about 5 mm thick. The criteria to be remembered is that it must be sufficiently thin to allow enough ammonia to diffuse to the back side of the membrane 24 so that an indicator color change is detectable through the handle of test strip 10. The test is read through the back side to avoid any interference from the highly alkaline water coming in contact with the indicators.

The membrane 24 is coated on both sides with an excess of a composition which will adhere an indicator system to membrane 24 of indicator pad 16. Any indicator system that will responsively and discriminatingly change color in the presence of contact with ammonia and has some hydrophobicity can be used. The terms responsively and discriminatingly mean that a color change in fact occurs, and that depending upon the concentration of ammonia, gradients of color intensity can be achieved to indicate concentrations on a parts per million level of ammonia (see FIG. 5). One suitable indicator mixture is bromophenol blue (free acid), bromocresol green, sodium salt, and bromocresol purple (free acid) as pH indicators. Each indicator undergoes a color change from yellow to green at differing pH intervals, except for bromocresol purple, which changes from yellow to purple. Bromophenol blue and bromocresol green, and the sodium salts of each are balanced to give the needed sensitivity, while addition of the bromocresol purple aids resolution at the higher ammonia concentration levels. Possible indicators, used alone or in mixtures, include but are not limited to Bromophenol Blue, Xylenol Blue, Bromocresol Purple, Tetrabromophenolphthalein Ethyl Ester, Bromocresol Green, Ethyl Red, Chlorophenol Red, Congo Red, Thymol Blue, Tetraiodophenolsulfonephthalein, Tetrabromophenol Blue, and Methyl Red.

4-(Tert-Octyl)phenol facilitates penetration of the membrane by the indicators and also coats the membrane. Brij® 76 is a surfactant which assists in coating the membrane and transporting the ammonia through the membrane. Ethyl cellulose acts as a stabilizer for both the indicators and the (tert-octyl) phenol. The addition of ethyl cellulose also helps to control the water breakthrough interference by enhancing the hydrophobicity of the matrix.

EXAMPLES

The following examples are offered to further illustrate but not limit the process of the present invention. In the examples test strips in accordance with the above description were prepared and then tested against known concentrations of ammonia in order to validate the testing.

The polystyrene material used for the handle was purchased from American National Can. Soda lime pad 14 was a 0.2 inch by 0.4 inch reagent pad having a weight percent of sodium hydroxide of 9.54%, and it was a weight percent of calcium carbonate at 0.12%.

The hydrophobic membrane of indicator pad 16 was a polypropylene membrane, naturally hydrophobic obtained from Cuno Filter Systems with a pore size of 0.6 microns. It was coated with a pH indicator dye/adhesive mixture with ethyl cellulose of reagent solution having the following concentrations:

TABLE I

| DESCRIPTION | 1X MASTER |
|---|---|
| (tert-octyl) phenol | 130 g |
| bromophenol blue (free acid) | 0.65 g |
| bromocresol green, Sodium Salt | 1.70 g |
| bromocresol purple (free acid) | 0.34 g |
| reagent alcohol | 213 g (270 ml) |
| Brij 76 | 1.50 g |
| toluene | 520 g (600 ml) |
| ethyl cellulose - 4 | 12.9 g |

Test strips 12 were then used in the testing. Test tube 28 was filled with ammonia standard solutions to the level of approximately 3 ml. Test strip 12 was vigorously moved up and down in the water sample for 30 seconds, making sure that all pads were submerged. The test strip was removed, and excess water shaken off. 30 seconds was allowed to pass for color to fully develop. The test strip was then held with the pads facing away from the person conducting the test and read on the small end pad 22 through the back of the plastic strip 12. It was then compared to a color chart (see FIG. 5) and the results recorded. Accuracy comparisons are shown in the table below indicating good correlation, and that the test worked and performed all the stated objectives of the present invention.

TABLE II

| Ammonia Concentration | | Ammonia Concentration | | Ammonia Concentration | | Ammonia Concentration | | Ammonia Concentration | | Ammonia Concentration | |
|---|---|---|---|---|---|---|---|---|---|---|---|
| Nominal | Test Strip | Nominal | Test Strip | Nominal | Test Strip | Nominal | Test Strip | Nominal | Test Strip | Nominal | Test Strip |
| 0 | 0 | 0.25 | 0.08 | 0.5 | 0.38 | 1.0 | 1.0 | 3.0 | 3.0 | 6.0 | 6.0 |
| 0 | 0 | 0.25 | 0.12 | 0.5 | 0.38 | 1.0 | 1.0 | 3.0 | 3.0 | 6.0 | 6.0 |
| 0 | 0 | 0.25 | 0.20 | 0.5 | 0.30 | 1.0 | 1.0 | 3.0 | 2.6 | 6.0 | 6.0 |
| 0 | 0 | 0.25 | 0.38 | 0.5 | 0.45 | 1.0 | 1.0 | 3.0 | 4.5 | 6.0 | 6.0 |
| 0 | 0 | 0.25 | 0.25 | 0.5 | 0.45 | 1.0 | 1.0 | 3.0 | 3.0 | 6.0 | 6.0 |
| 0 | 0 | 0.25 | 0.23 | 0.5 | 0.42 | 1.0 | 1.0 | 3.0 | 3.6 | 6.0 | 6.0 |
| 0 | 0 | 0.25 | 0.25 | 0.5 | 0.45 | 1.0 | 0.85 | 3.0 | 3.0 | 6.0 | 5.7 |
| 0 | 0 | 0.25 | 0.25 | 0.5 | 0.42 | 1.0 | 0.95 | 3.0 | 3.0 | 6.0 | 6.0 |
| 0 | 0 | 0.25 | 0.25 | 0.5 | 0.45 | 1.0 | 0.95 | 3.0 | 3.0 | 6.0 | 6.0 |
| 0 | 0 | 0.25 | 0.20 | 0.5 | 0.50 | 1.0 | 0.85 | 3.0 | 3.0 | 6.0 | 6.0 |
| 0 | 0 | 0.25 | 0.25 | 0.5 | 0.45 | 1.0 | 1.0 | 3.0 | 4.2 | 6.0 | 6.0 |
| 0 | 0 | 0.25 | 0.25 | 0.5 | 0.50 | 1.0 | 1.0 | 3.0 | 3.0 | 6.0 | 6.0 |
| 0 | 0 | 0.25 | 0.27 | 0.5 | 0.50 | 1.0 | 1.0 | 3.0 | 3.9 | 6.0 | 6.0 |
| 0 | 0 | 0.25 | 0.12 | 0.5 | 0.38 | 1.0 | 1.0 | 3.0 | 3.0 | 6.0 | 6.0 |
| 0 | 0 | 0.25 | 0.23 | 0.5 | 0.38 | 1.0 | 1.0 | 3.0 | 4.2 | 6.0 | 6.0 |
| 0 | 0 | 0.25 | 0.25 | 0.5 | 0.45 | 1.0 | 0.65 | 3.0 | 6.0 | 6.0 | 6.0 |
| 0 | 0 | 0.25 | 0.15 | 0.5 | 0.42 | 1.0 | 0.65 | 3.0 | 3.0 | 6.0 | 6.0 |
| 0 | 0 | 0.25 | 0.25 | 0.5 | 0.50 | 1.0 | 0.60 | 3.0 | 3.0 | 6.0 | 6.0 |
| 0 | 0 | 0.25 | 0.25 | 0.5 | 0.50 | 1.0 | 0.85 | 3.0 | 3.0 | 6.0 | 5.7 |
| 0 | 0 | 0.25 | 0.25 | 0.5 | 0.45 | 1.0 | 1.0 | 3.0 | 3.0 | 6.0 | 6.0 |
| 0 | 0 | 0.25 | 0.23 | 0.5 | 0.50 | 1.0 | 0.85 | 3.0 | 3.0 | 6.0 | 6.0 |
| 0 | 0 | 0.25 | 0.25 | 0.5 | 0.45 | 1.0 | 0.90 | 3.0 | 3.0 | 6.0 | 6.0 |
| 0 | 0 | 0.25 | 0.25 | 0.5 | 0.40 | 1.0 | 0.85 | 3.0 | 3.0 | 6.0 | 6.0 |
| 0 | 0 | 0.25 | 0.25 | 0.5 | 0.50 | 1.0 | 0.90 | 3.0 | 3.0 | 6.0 | 6.0 |
| 0 | 0 | 0.25 | 0.25 | 0.5 | 0.50 | 1.0 | 0.90 | 3.0 | 3.0 | 6.0 | 6.0 |
| 0 | 0 | 0.25 | 0.25 | 0.5 | 0.50 | 1.0 | 0.90 | 3.0 | 3.0 | 6.0 | 6.0 |
| 0 | 0 | 0.25 | 0.25 | 0.5 | 0.50 | 1.0 | 1.00 | 3.0 | 3.0 | 6.0 | 6.0 |
| 0 | 0 | 0.25 | 0.25 | 0.5 | 0.50 | 1.0 | 0.75 | 3.0 | 3.0 | 6.0 | 6.0 |
| 0 | 0 | 0.25 | 0.25 | 0.5 | 0.50 | 1.0 | 0.75 | 3.0 | 3.0 | 6.0 | 6.0 |
| 0 | 0 | 0.25 | 0.25 | 0.5 | 0.50 | 1.0 | 0.85 | 3.0 | 3.0 | 6.0 | 3.6 |
| 0 | 0 | 0.25 | 0.25 | 0.5 | 0.50 | 1.0 | 0.70 | 3.0 | 3.0 | 6.0 | 6.0 |
| 0 | 0 | 0.25 | 0.25 | 0.5 | 0.45 | 1.0 | 0.90 | 3.0 | 3.0 | 6.0 | 6.0 |
| 0 | 0 | 0.25 | 0.25 | 0.5 | 0.50 | 1.0 | 0.75 | 3.0 | 3.0 | 6.0 | 6.0 |
| 0 | 0 | 0.25 | 0.25 | 0.5 | 0.50 | 1.0 | 0.75 | 3.0 | 3.0 | 6.0 | 6.0 |
| 0 | 0 | 0.25 | 0.25 | 0.5 | 0.45 | 1.0 | 0.95 | 3.0 | 4.5 | 6.0 | 6.0 |
| 0 | 0 | 0.25 | 0.23 | 0.5 | 0.45 | 1.0 | 0.90 | 3.0 | 3.0 | 6.0 | 6.0 |

TABLE II-continued

| | | SUMMARY VALUES | | | |
|---|---|---|---|---|---|
| Max | 0.38 | 0.50 | 1.0 | 6.0 | 6.0 |
| Min | 0.08 | 0.30 | 0.60 | 2.6 | 3.6 |
| Ave | 0.23 | 0.46 | 0.89 | 3.3 | 5.9 |
| Std. Dev | 0.050 | 0.050 | 0.122 | 0.659 | 0.403 |

What is claimed is:

1. A method of detecting ammonia in aqueous systems, such as aquarium water, comprising:
    obtaining a defined sample volume of the water to be tested;
    contacting the defined sample volume of water with a non-ammonia alkaline agent to raise the pH to at least 10;
    simultaneously contacting said sample volume of water with an indicator pad comprising a porous hydrophobic barrier membrane having a front side and an opposite side and capable of allowing ammonia to pass through from said front side to said opposite side of said membrane;
    said membrane being coated with an excess of a pH chromogenic indicator mixture which responsively changes color upon contact with ammonia, and said membrane being impregnated with ethyl cellulose, a surfacant, and tertiary octyl phenol;
    observing the indicator color response on the opposite side of said membrane; and thereafter,
    comparing the observed intensity of the color response with standard color chart to determine ammonia concentration of said water sample.

2. The method of claim 1 wherein the membrane is affixed to a semi-rigid handle with the opposite side of the membrane being in juxtaposition with the handle.

3. The method of claim 2 wherein the excess pH chromogenic indicator mixture, in addition to being incorporated in the membrane, comprises a thin layer thereof on at least the opposite side of the membrane.

4. The method of claim 2 wherein the excess pH chromogenic indicator mixture, in addition to being incorporated in the membrane, comprises thin layers thereof on both the front and opposite sides of the membrane.

5. The method of claim 1 wherein the non-ammonia alkaline agent comprises an alkalizing pad and the alkalizing pad and porous hydrophobic barrier membrane are affixed to clear semi-rigid handle.

6. The method of claim 1 wherein the non-ammonia alkaline agent is a mix of calcium hydroxide, sodium hydroxide, and carbonates of calcium hydroxide and sodium hydroxide.

7. The method of claim 1 wherein the porous hydrophobic barrier membrane is an inert polypropylene matrix.

8. The method of claim 7 wherein the hydrophobic barrier membrane has a porosity of from 0.2 microns to 2.5 microns.

9. The method of claim 8 wherein the hydrophobic membrane has a porosity of 0.6 microns to 1.2 microns.

10. The method of claim 7 wherein the indicator mixture is a mixed indicator which is both responsive and discriminating in degrees of intensity to increasing levels of ammonia concentration.

11. The method of claim 10 wherein the mixed indicator comprises of bromophenol blue, bromocresol green, sodium salt and bromocresol purple, and undergoes a color change from yellow to green at differing pH levels.

12. A test device for detecting ammonia production potential of aqueous systems comprising:
    a test strip comprising a clear semi-rigid material,
    an alkalizing pad adhered to the test strip, the alkalizing pad comprising a non-ammonia alkaline agent sufficient to raise the pH of a confined test sample to at least 10; and
    an indicator pad adhered to the test strip, the indicator pad comprising a porous hydrophobic barrier membrane that allows ammonia gas to pass through, the porous hydrophobic barrier membrane having a front side for contacting the test sample and an opposite side coated with a pH chromogenic mixture which responsively changes color in response to the amount of ammonia gas in the aqueous system, said membrane being impregnated with ethyl cellulose, a surfacant, and tertiary octyl phenol, and the opposite side protected from contact with the test sample by the clear semi-rigid material,
    wherein color changes of the pH chromogenic mixture on the opposite side of the membrane may be viewed through the clear semi-rigid material.

* * * * *

UNITED STATES PATENT AND TRADEMARK OFFICE
CERTIFICATE OF CORRECTION

| | |
|---|---|
| PATENT NO. | : 7,033,839 B1 |
| APPLICATION NO. | : 09/268930 |
| DATED | : April 25, 2006 |
| INVENTOR(S) | : Lydia J. Dobler, Jean M. Gibbons and Vladimir Yu Evtodienko |

It is certified that error appears in the above-identified patent and that said Letters Patent is hereby corrected as shown below:

Claim 1, column 7, line 28, correct "surfacant" to -- surfactant --.

Claim 1, column 7, line 32, after the word "with" and before the word "standard," insert -- a --.

Claim 12, column 8, line 44, correct "surfacant" to -- surfactant --.

Signed and Sealed this

Second Day of January, 2007

JON W. DUDAS
*Director of the United States Patent and Trademark Office*